United States Patent
Richard et al.

[11] Patent Number: 6,041,780
[45] Date of Patent: Mar. 28, 2000

[54] PRESSURE CONTROL FOR CONSTANT MINUTE VOLUME

[76] Inventors: Ron F. Richard, 12818 Reeder St., Overland Park, Kans. 66213; Aaron J. Dirks, 5704 W. 101 Ter., Overland Park, Kans. 66207; Stuart P. Williams, 14613 W. 91 Ter., Lenexa, Kans. 66215

[21] Appl. No.: 08/821,708

[22] Filed: Mar. 19, 1997

Related U.S. Application Data

[63] Continuation of application No. 08/475,561, Jun. 7, 1995, abandoned.

[51] Int. Cl.$^7$ .............................. A61M 16/00; A62B 7/00
[52] U.S. Cl. .............................. 128/204.18; 128/204.21; 128/204.23
[58] Field of Search .................. 128/204.18, 204.21, 128/204.23, 205.24

[56] References Cited

U.S. PATENT DOCUMENTS

| | | | |
|---|---|---|---|
| 3,741,208 | 6/1973 | Jonsson et al. | 128/204.18 |
| 3,923,056 | 12/1975 | Bingmann et al. | 128/204.18 |
| 3,961,627 | 6/1976 | Ernst et al. | 128/204.18 |
| 4,323,064 | 4/1982 | Hoenig et al. | 128/204.21 |
| 4,340,044 | 7/1982 | Levy et al. | 128/204.21 |
| 4,365,636 | 12/1982 | Barker | 128/716 |
| 4,421,044 | 12/1983 | Gedeon et al. | 128/204.23 |
| 4,421,113 | 12/1983 | Gedeon et al. | 128/204.23 |
| 4,440,177 | 4/1984 | Anderson et al. | 128/719 |
| 4,506,666 | 3/1985 | Durkan | 128/204.23 |
| 4,596,247 | 6/1986 | Whitwam et al. | 128/204.25 |
| 4,637,385 | 1/1987 | Rusz | 128/204.21 |
| 4,644,947 | 2/1987 | Whitwam et al. | 128/204.25 |
| 4,655,213 | 4/1987 | Rapoport et al. | 128/205.25 |
| 4,928,684 | 5/1990 | Breitenfelder et al. | 128/204.21 |
| 4,944,310 | 7/1990 | Sullivan | 128/848 |
| 4,957,107 | 9/1990 | Sipin | 128/204.21 |
| 5,129,390 | 7/1992 | Chopin et al. | 128/204.21 |
| 5,134,995 | 8/1992 | Gruenke et al. | 128/204.23 |
| 5,245,995 | 9/1993 | Sullivan et al. | 128/204.23 |
| 5,335,654 | 8/1994 | Rapoport | 128/204.23 |
| 5,353,788 | 10/1994 | Miles | 128/204.23 |
| 5,385,142 | 1/1995 | Brady et al. | 128/204.23 |
| 5,423,870 | 6/1995 | Olive et al. | 607/18 |
| 5,458,137 | 10/1995 | Axe et al. | 128/204.23 |
| 5,483,969 | 1/1996 | Testerman et al. | 128/716 |
| 5,494,028 | 2/1996 | DeVries et al. | 128/205.24 |
| 5,537,997 | 7/1996 | Mechlenburg et al. | 128/204.23 |
| 5,540,219 | 7/1996 | Mechlenburg et al. | 128/204.23 |
| 5,582,163 | 12/1996 | Bonassa | 128/204.26 |
| 5,598,838 | 2/1997 | Servidio et al. | 128/204.23 |
| 5,752,509 | 5/1998 | Lachmann et al. | 128/204.23 |
| 5,797,393 | 8/1998 | Kohl | 128/204.23 |

FOREIGN PATENT DOCUMENTS

| | | |
|---|---|---|
| 0 459 647 A2 | 5/1991 | European Pat. Off. . |
| 94308139 | 5/1995 | European Pat. Off. ........ A61B 5/113 |
| 2 596 279 | 3/1986 | France . |
| 2 663 547 | 6/1990 | France . |
| WO 93/09834 | 5/1993 | WIPO . |

OTHER PUBLICATIONS

"Automatic Ventilation of the Lungs", Mushin, Blackwell Scientific Publications, 1990, pp. 770–775.

Sullivan et al., Home Treatment of Obstructive Sleep Apnea With Continuous Postive Airway Pressure Applied Through A Nose Mask, 1984, pp. 49–54.

Respironics, Inc., Virtuoso Smart CPAP System, 1995, pp. 1–4.

*Primary Examiner*—John G. Weiss
*Assistant Examiner*—Joseph F. Weiss, Jr.
*Attorney, Agent, or Firm*—Fulwider Patton Lee & Utecht, LLP

[57] ABSTRACT

A method and apparatus for ventilating a patient wherein the inspiratory positive airway pressure (IPAP) is adjusted as a function of minute volume. The IPAP is gradually adjusted over extended periods of time in small increments to conform the patient's minute volume to a prescribed value. This gentle but effective approach ensures adequate ventilation while minimizing discomfort to the patient thereby rendering the system ideal for treating sleep disordered breathing in the homecare environment.

12 Claims, 4 Drawing Sheets

PRESSURE CONTROL FOR CONSTANT MINUTE VOLUME

This application is a continuation of application Ser. No. 08/475,561 filed on Jun. 7, 1995 abandoned.

BACKGROUND OF THE INVENTION

The present invention generally relates to ventilator systems that are used in assisting the respiration of a patient to treat disturbed breathing, snoring, mixed obstructive sleep apnea, and certain cardiovascular sleep conditions. More particularly, the present invention pertains to the control of the air pressure to which the patient is subjected to by the ventilator during each respiratory cycle to provide a system well-suited for homecare applications.

Obstructive sleep apnea is a sleep disorder characterized by the relaxation of the airway, including the upper airway muscle tissue during sleep. When this occurs, the relaxed muscles can partially or completely block the patient's airway, a condition more prevalent in overweight patients. Partial blockage can result in snoring while complete blockage can result in sleep apnea. When complete blockage occurs, the patient's ventilation efforts do not result in the intake of air and the patient becomes oxygen deprived. In reaction, the patient begins to awaken and upon reaching a nearly awakened state, the upper airway muscles resume normal tension which clears the airway and allows inhalation to occur. The patient then falls back to the deeper sleep whereupon the upper airway muscles again relax and the apneic cycle repeats. Central apnea is a condition wherein no inspiratory effort occurs or is delayed. Both central apnea as well as obstructive sleep apnea may be as present simultaneously, a condition referred to as mixed apnea. Other breathing irregularities are known which involve apneic intervals, Cheyne-Stokes breathing, being an example thereof.

In some patients, sleep apnea events can occur hundreds of times during a sleep session. As a consequence of the repetitive arousal to the nearly awakened state, the patient never achieves fully relaxed deep sleep and is deprived of REM (rapid eye movement) sleep. Additionally, the patient's blood oxygen falls to subnormal levels. People afflicted with sleep apnea are continually tired even after an apparently normal night's sleep, while the continual or repeated oxygen depravation may have an adverse affect on the patient's cardiovascular system.

In order to treat obstructive sleep apnea, so-called continuous positive airway pressure (CPAP) systems have been devised in which prescribed levels of positive airway pressure are continuously imposed on the patient's airway. The presence of such positive pressures within the airway provides a pressure splint to offset the negative inspiratory pressure thereby maintaining tissue in position and the patient's airway open. The positive pressure is typically generated by a blower, the output of which is ducted to the patient and connected to the airway by a nasal pillow which seals with the patient's nares. Control valves in the system control the pressure to which the patient's airway is subjected.

In prescribing the CPAP therapy, it is usually necessary for a patient to spend one or two nights in a sleep treatment laboratory where it is first determined whether the patient has a respiratory disorder such as sleep apnea. If so, the patient is then fitted with a CPAP device whereupon pressure and volume parameters are determined for providing the necessary air splint and satisfying the patient's respiratory requirements.

A number of shortcomings, are associated with the previously known CPAP systems. Two fundamentally different approaches have heretofore been taken with respect to the manner in which the breathing is controlled each suffering from a number of disadvantages. Initially, ventilator systems were designed to deliver a predetermined volume during the inspiration phase of each breathing cycle. While this approach positively ensures adequate respiration even for patients completely incapable of breathing on their own, the rigorous routine is perceived as quite uncomfortable by patients requiring less breathing assistance. The prescribed volume of air is after all forced into the patient's airways without regard to the pressures that may be generated and independent of what rate the patient would consider comfortable. Such systems are therefore not well matched to the needs of the homecare market, especially in the treatment of sleep disordered breathing, and are today reserved exclusively for very critical care applications.

Substantially more comfortable breathing assistance is provided by ventilator systems wherein the respiratory cycle is pressure driven. Such systems may be configured to supply air at a predetermined inspiratory positive airway pressure (IPAP) upon sensing the onset of inspiration and until the patient initiates exhalation. Upon exhalation, system pressure is immediately reduced to a predetermined expiratory positive airway pressure (EPAP) to facilitate the expulsion of air from the patient's airway. This type of system augments a patient's spontaneous tidal volumes and was the accepted mode for assisting the patient to overcome the work of breathing associated with an artificial airway, the mechanics of the ventilator and for the weaning of the patient from the full support of mechanical ventilation. In its simplest form, such system does not take into account the actual volume of air respirated by the patient. Consequently, despite satisfying the prescribed pressure parameters, the patient may nonetheless suffer from hypoventilation, reduced $PAO_2$, reduction in daytime alertness and increased $CO_2$ levels.

More recently, several hybrid forms of pressure support have been introduced which vary in method and adjustment but strive to overcome the problem associated with varying tidal volumes using pressure limited modes of ventilation. One way of accomplishing this is to vary the amount of pressure to achieve satisfactory gas exchange in light of changing compliance/resistance components by estimating or actually monitoring such parameters. Since such approach may still require fairly close monitoring of the patient in order to avoid hypoventilation and the consequences thereof, many of the corresponding devices are still better suited for use in hospitals rather than in the homecare environment. U.S. Pat. No. 5,134,995, which discloses a variety of systems that undertake to adjust air pressure to accommodate various conditions, is hereby incorporated by reference.

A system is needed that ensures adequate ventilation of a patient while eliminating the need for monitoring and supervision so as to provide a device suited for the homecare market. Previously known systems have been unable to adequately satisfy this need.

SUMMARY OF THE INVENTION

The present invention overcomes the disadvantages associated with the prior art CPAP devices by providing for the automatic adjustment of the pressure support level in order to ensure that adequate ventilation is achieved. Only minimal monitoring of the patient is necessary thereby rendering the system ideally suited for homecare applications.

The system of the present invention provides ventilation by supplying air at elevated pressure during the inspiration phase of the respiratory cycle. The pressure level (IPAP) is set as a function of the patient's actual minute volume in relation to a preselected minute volume target wherein minute volume is defined as the total volume of air respirated over the course of a minute. As a result, adequa ventilation is readily achieved despite fluctuations in the patient's respiration rate, compliance and resistance and without the disadvantage s associated with prior art devices.

A target minute volume is initially prescribed based on various physiological parameters of the patient. An initial baseline IPAP is then calculated as a function of a such prescribed minute volume, the anticipated breath rate and nominal compliance and resistance values. Upon being subjected to ventilation, the actual minute volume respirated by the patient is calculated, which in turn is compared with the prescribed minute volume pursuant to which the IPAP is gradually adjusted in order to reconcile the actual value with the prescribed value. The adjustment of the IPAP is very gradual both in terms of the frequency of adjustments as well as the magnitude of such adjustments in order not to arouse the patient while sleeping. Adequate ventilation is ensured because the system's function is ultimately based on the volume of air that is actually respirated.

These and other features and advantages of the present invention will become apparent from the following detailed description of a preferred embodiment which, taken in conjunction with the accompanying drawings, illustrates by way of example the principles of the invention.

DETAILED DESCRIPTION OF THE PREFERRED EMBODIMENT

The ventilation system of the present invention provides a method and apparatus for automatically adjusting the IPAP supplied to a patient during the inspiration phase of each respiratory cycle. The automatic operation ensures that the patient is adequately ventilated while the manner in which such function is achieved is sufficiently subtle so as not to awaken a sleeping patient which is, of course, essential in the treatment of sleep disordered breathing.

Figure 1:
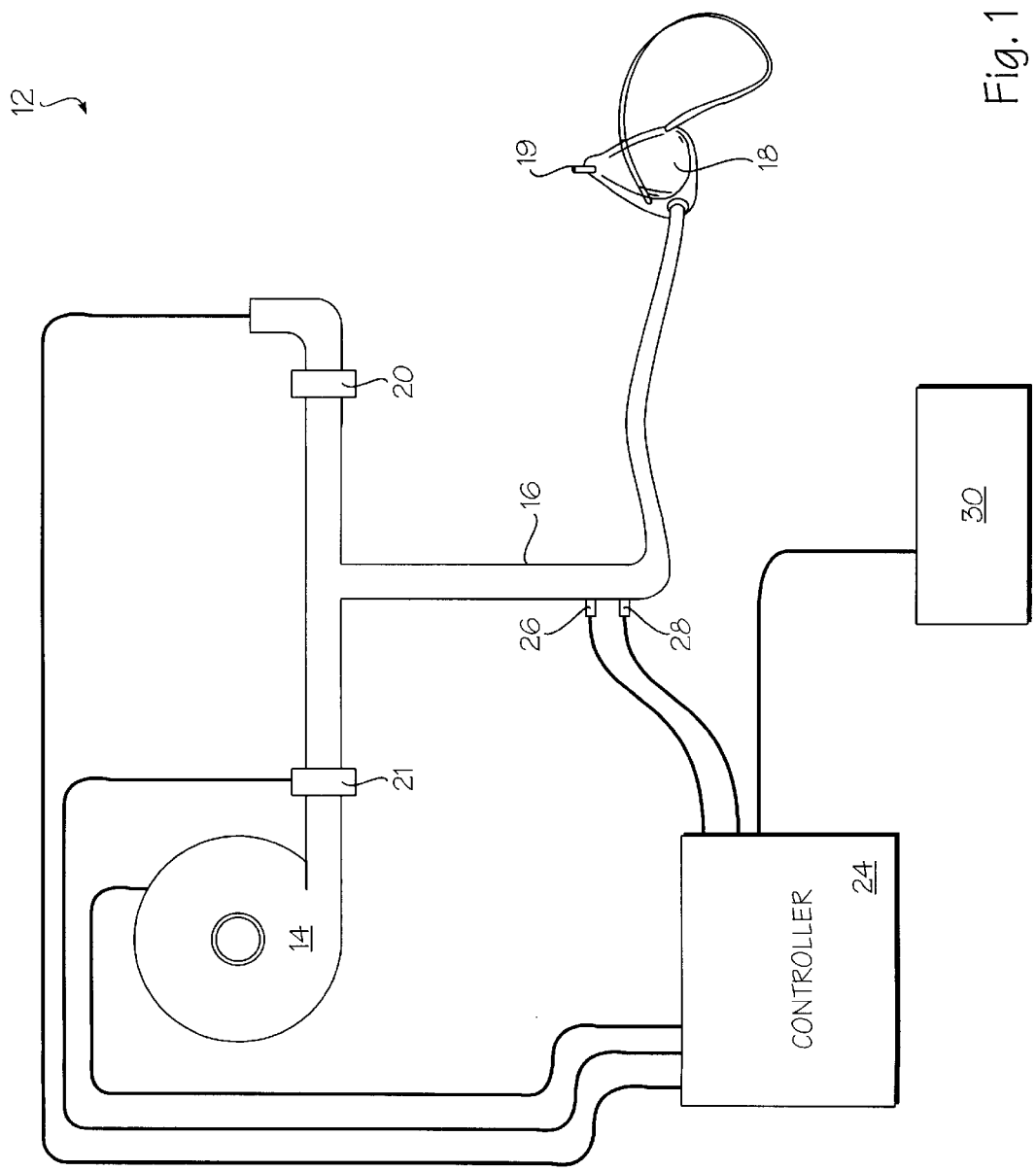
FIG. 1 is a schematic representation of the ventilation system of the present invention.

FIG. 1 provides a schematic representation of the system 12 of the present invention in its most fundamental form. A blower 14 pressurizes the system with fresh air. Conduit 16 ducts such pressurized air to a standard nasal mask 18 which is fitted about the nose or a nasal pillow that is fitted to the nose and extends directly into the patient's nares. Port 19 continuously vents a small amount of air from the nasal mask or pillow in order to prevent moisture buildup and subsequent condensation therein. The port also prevents buildup of exhaled gases including $CO_2$. The actual pressure within the system is controlled by relief valve 20 which vents superfluous air volume to the atmosphere. The position of the relief valve is in turn controlled by controller 24 pursuant to a number of different signals. Flow meter 26 provides information as to the volume of air inhaled by the patient, while pressure sensor 28 provides information as to the pressurization of the system at any given moment. The function of the controller is additionally subject to various parameters that are input such as through keyboard 30. The controller is also operative to control the position of valve 21 which is closed when relief valve 20 is opened and to tailor the output of blower 14 in relation to pressure demands.

The general function of the ventilator entails oscillating the system pressure between an IPAP value and a much lower EPAP value during the inhalation and expiration phase, respectively, of each respiratory cycle. The device senses the onset of each phase and immediately adjusts the airway pressure accordingly. Consequently, the IPAP serves to maintain a positive pressure in the patient's airway in order to avoid the negative pressure that would result pursuant to the patient's inspiratory efforts thereby splinting the otherwise obstructive tissue into position. The reduction of pressure to the EPAP minimizes the work the patient must expend in order to exhale.

Additionally, the system monitors the tidal volume of each cycle and more particularly the sum of the tidal volumes over a given period of time to calculate the minute volume. The calculated value is compared with a target to determine whether an insufficient or an excessive volume of air is being respirated. In the event the actual minute volume exceeds the target value, the IPAP is gradually reduced such as by a small increment every few minutes. If, on the other hand, the actual minute volume is less than the target value, the IPAP is gradually increased, again by a small increment every few minutes.

Figure 2A:
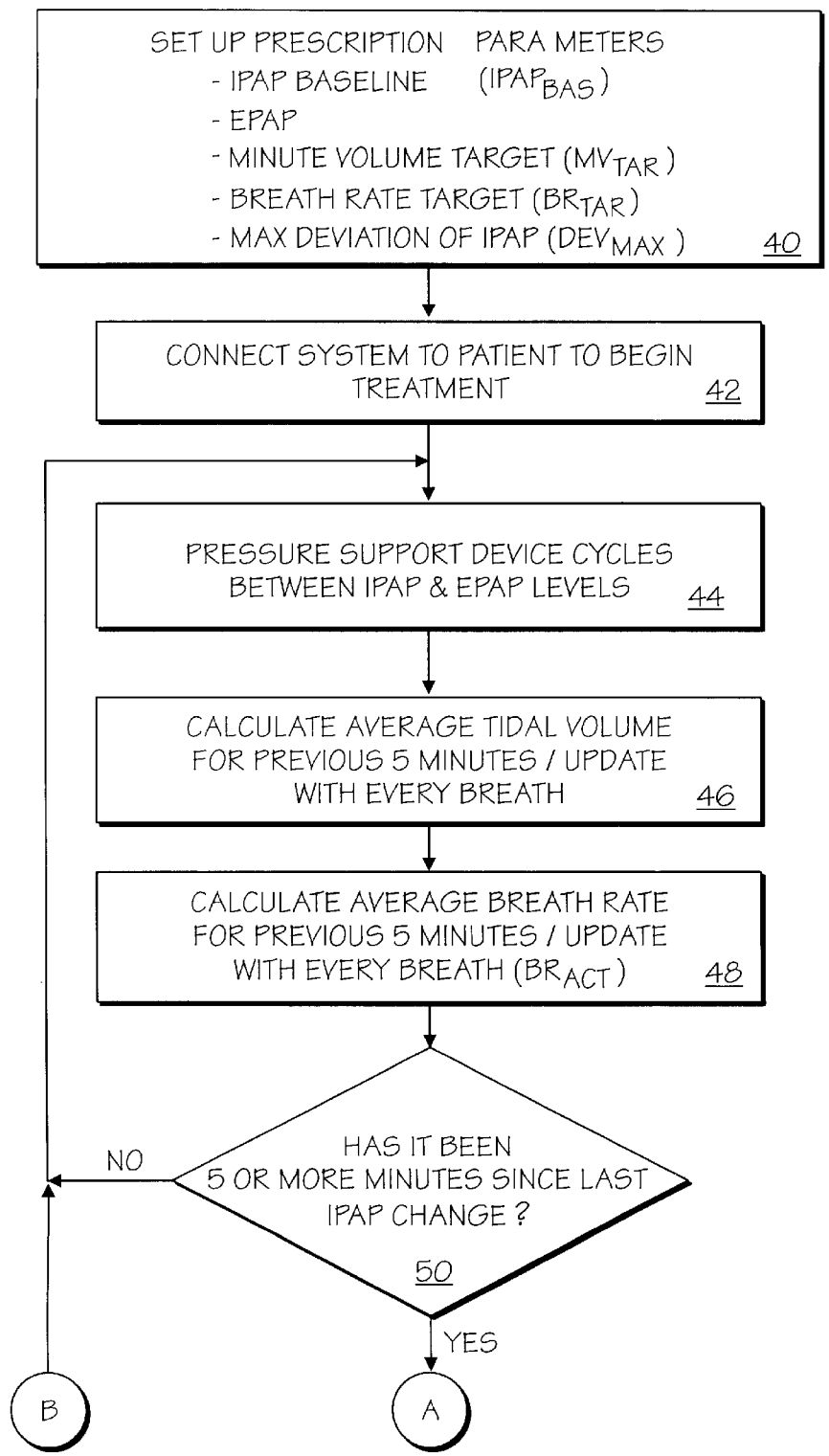
FIGS. 2a–c are a flowchart of the steps employed in adjusting the function of the ventilator of the present invention.
Figure 2B:
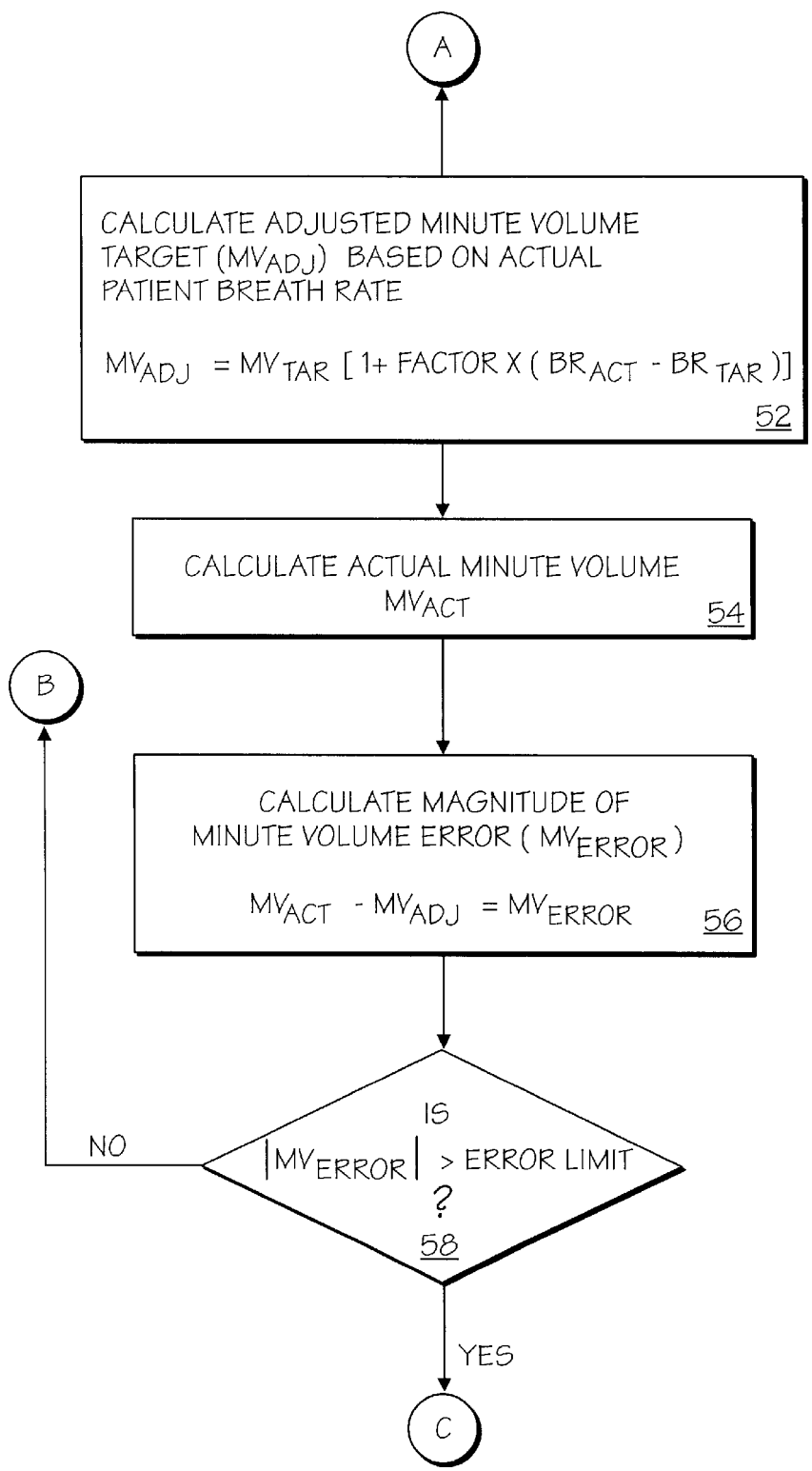
Figure 2C:
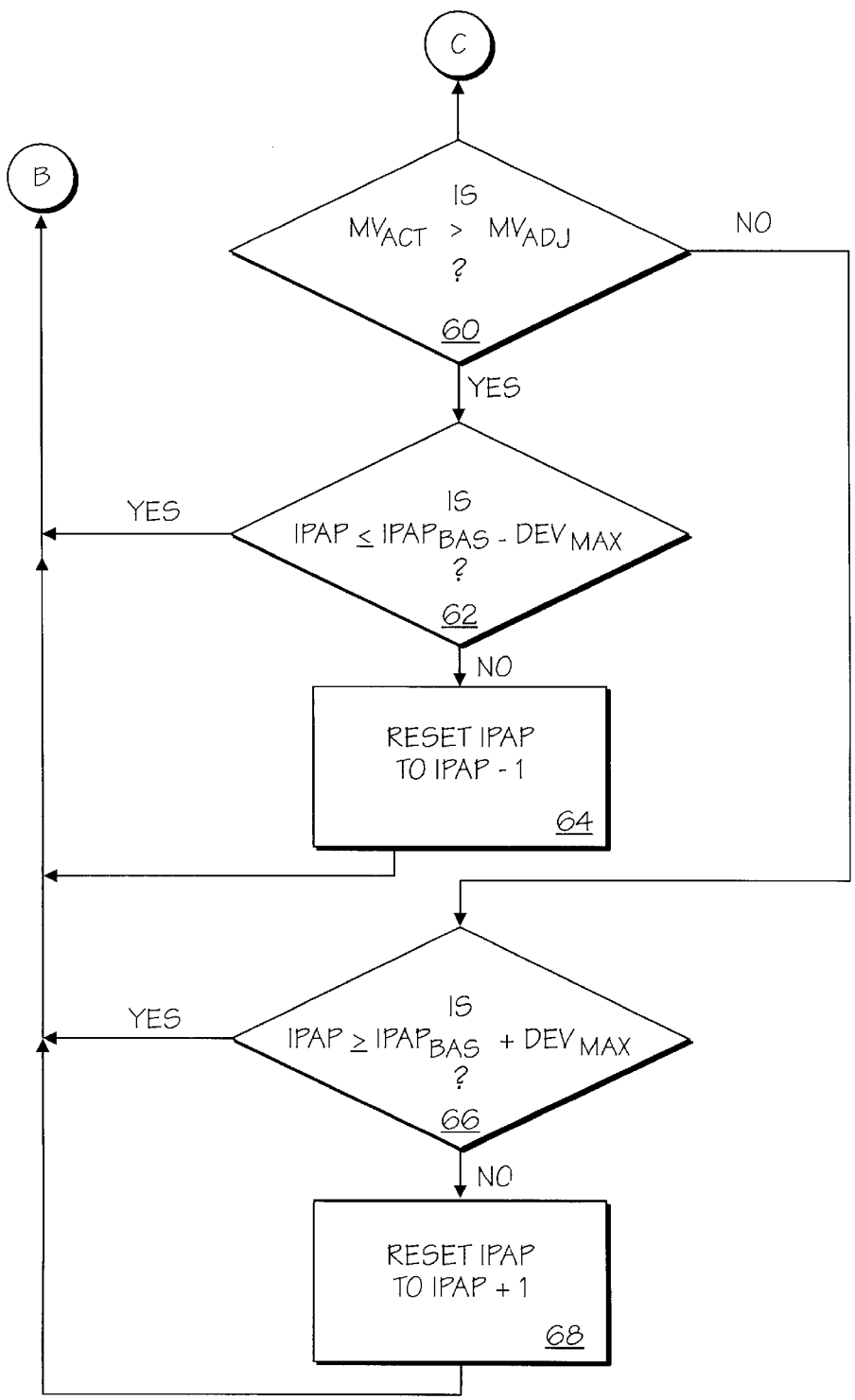

The flowchart shown in FIGS. 2a–c illustrates in detail the method by which the system automatically adjusts the IPAP. By considering various physiological parameters, the sleep professional first determines a minute volume target and breath rate target for a particular patient along with the EPAP, the initial IPAP and the maximum deviation from IPAP. These values are input into the controller 24 via keyboard 30 at step 40. The nasal mask or pillow 18 is then fitted to the patient's nose and treatment is commenced at step 42. At step 44, the blower motor 14 is energized and the relief valve 20 is actuated to maintain the initial IPAP setting during inhalation and the EPAP setting during exhalation. The onset of each respiratory phase is sensed by methods well known in the art.

As ventilation continues, the tidal volumes respired by the patient are averaged over the previous 5 minutes and updated with every breath at step 46. This calculation must also take into consideration an initial adjustment factor indicative of the volume escaping through port 19 and any miscellaneous leakage occurring throughout the system. Such information is provided by the output of flow meter 26 and an internal clock (not shown). The average breath rate is then calculated at step 48 by dividing the number of breath cycles sensed by flow sensor 26 by the elapsed time. At step 50, it is determined whether 5 minutes have expired since the last IPAP change. If not, the system continues to function at the initial IPAP setting, if more than 5 minutes have come to pass, the program moves on to the subroutine shown in FIG. 2b.

At step 52, the target minute volume is adjusted as a function of the breath rate. This is necessary as the tidal volume and the efficiency of air exchange in the lungs is linked to the respiration rate. A typical adjustment factor used in this calculation is FACTOR=[0.0375×breaths/minute] +0.55. The two coefficients may vary as a function of patient parameters and are individually entered via keyboard 30. In the succeeding step, step 54, the patient's actual minute volume is calculated by taking the average tidal volume obtained in step 46 and multiplying it by the breath rate obtained in step 48. The actual minute volume is then compared to the adjusted minute volume at step 56 and in the event such calculated error is less than a preselected error limit, no adjustment of the IPAP is deemed necessary and the system continues to cycle at the initially set levels. If on the other hand, the preselected error limit is exceeded, an adjustment of the IPAP is necessary. At step 60, it is determined whether the actual minute volume exceeds the adjusted minute volume. If not, the program skips to step 66. If so, a determination is made at step 62, as to whether the IPAP is already less than a preselected minimum value. If yes, no adjustment is made, if not then IPAP is reduced by a single increment, such as 1 cm $H_2O$. At step 66, the determination is made as to whether the IPAP exceeds a preselected maximum value. If so, no adjustment is made, if not, the IPAP is increased by a single increment such as 1 cm $H_2O$.

As a direct consequence of this approach to controlling a ventilation, the patient is assured of receiving sufficient oxygen. The system is flexible enough to allow for a change of breath rate and fluctuation of tidal volume from breath to breath. When a change in IPAP is deemed necessary, the change is made gradually, i.e. varied in small increments and spread out over time to provide for a fairly transparent operation. This is, of course, essential in treating sleep apnea as any arousal from sleep, or other sleep disorder breathing would defeat the purpose of the treatment.

While a particular form of the invention has been illustrated and described, it will also be apparent to those skilled in the art that various modifications can be made without departing from the spirit and scope of the invention. Various types of ventilation systems may be used, additional factors may be taken into consideration in adjusting the various target values and limits and features may be incorporated to accommodate certain contingencies. Accordingly, it is not intended that the invention be limited except by the appended claims.

We claim:

1. A method for automatically adjusting IPAP during ventilation of a patient being assisted by a system having a controller, comprising the steps of:

maintaining a constant preselected IPAP level during each inspiratory phase;

preselecting a target minute volume;

continually measuring said patient's actual minute volume;

providing information as to said measured actual minute volume to said controller; and periodically adjusting said preselected IPAP level of subsequent inspiratory phases so as to gradually conform the actual minute volume to the target minute volume.

2. The method of claim 1 wherein said adjusting step is carried out at preselected time intervals and in preselected pressure increments.

3. The method of claim 2 wherein said preselected time intervals comprise 3–5 minutes and said preselected pressure increments comprise 1 cm $H_2O$.

4. The method of claim 1 further comprising the steps of:

measuring the patient's respiration rate; and periodically adjusting the target minute volume to compensate for any changes in respiration rate.

5. The method of claim 4 wherein said periodic adjustment of the target minute volume is carried out at preselected time intervals.

6. The method of claim 5 wherein said preselected time intervals comprise about 5 minutes.

7. The method of claim 1 wherein the IPAP adjustment of the IPAP below a prescribed minimum IPAP and above a prescribed maximum IPAP is precluded.

8. The method of claim 1 wherein said adjusting step is facilitated by said controller.

9. The method of claim 1 wherein said information is provided by a flow meter.

10. An apparatus for providing breathing assistance to a patient comprising:

a source of pressurized air;

a conduit for ducting said pressurized air to said patient's airway;

a relief valve for maintaining a constant preselected level of air pressure of each inspiratory phase within said conduit;

a flow meter for measuring minute volume of air inhaled by the patient; and a controller for operating said relief valve to periodically adjust said preselected level of air pressure during subsequent inspiratory phases so as to cause the minute volume of air inhaled by the patient as measured by said flow meter to gradually conform to a preselected target value.

11. The apparatus of claim 10 wherein said controller operates said relief valve so to alter the air pressure by preselected increments over preselected time intervals.

12. The apparatus of claim 10 wherein said preselected target value is adjusted as a function of breath rate.

* * * * *